United States Patent [19]

Moore

[11] Patent Number: 5,111,547
[45] Date of Patent: May 12, 1992

[54] METHOD FOR FORMING PRECISION LIQUID/VAPOR SEPARATING BRISTLE ASSEMBLY

[75] Inventor: Boyd B. Moore, Houston, Tex.

[73] Assignee: Shell Oil Company, Houston, Tex.

[21] Appl. No.: 615,096

[22] Filed: Nov. 19, 1990

Related U.S. Application Data

[62] Division of Ser. No. 428,527, Oct. 30, 1989, Pat. No. 5,007,277.

[51] Int. Cl.$^5$ ................................................ A46B 3/00
[52] U.S. Cl. ........................................ 15/187; 55/462; 55/477
[58] Field of Search ............................... 55/183–188, 55/398, 443, 462, 464, 465, 477; 15/187

[56] References Cited

U.S. PATENT DOCUMENTS

| | | | |
|---|---|---|---|
| 2,795,807 | 6/1957 | Salvy | 15/187 |
| 2,796,047 | 6/1957 | Lehr | 15/187 |
| 2,922,489 | 1/1960 | Hollingsworth | 55/477 X |
| 2,993,565 | 7/1961 | Coulter | 55/462 X |
| 3,204,278 | 9/1965 | Lambros | 15/187 |
| 3,609,789 | 10/1971 | Slater | 15/187 |
| 4,736,627 | 4/1988 | Wicks et al. | 55/462 X |

FOREIGN PATENT DOCUMENTS 0216879  9/1907  Fed. Rep. of Germany ........ 55/464

*Primary Examiner*—Charles Hart

[57] ABSTRACT

A bristle assembly and method for making the same. The bristle assembly is particularly useful for forming into a brush-like arrangement for use in separating the liquid and vapor phases for determining the steam quality in a thermal injection well as described in U.S. Pat. No. 4,736,627.

5 Claims, 2 Drawing Sheets

METHOD FOR FORMING PRECISION LIQUID/VAPOR SEPARATING BRISTLE ASSEMBLY

This is a division of application Ser. No. 428,527, filed Oct. 30, 1989, now U.S. Pat. No. 5,007,277.

CROSS REFERENCE TO RELATED PATENT

The present application is related to U.S. Pat. No. 4,736,627 issued Apr. 12, 1988.

BACKGROUND OF THE INVENTION

The present invention relates to the production of liquid hydrocarbons and more particularly to the production of liquid hydrocarbons using in various thermal methods.

In recent years, as a result of decreasing reserves and increasing prices, the use of various thermal methods to produce heavy crude deposits has become economically attractive. In the most common thermal recovery process steam is injected by means of a well into the heavy crude deposit to reduce the viscosity thereof and allow the crude to be produced. Various methods have been used in thermal recovery, for example, in one method the steam is injected and the formation is allowed to soak and the crude drains into the well from which it is subsequently produced. In another method steam is used to drive the crude from one well toward another well. In all these cases it is desirable to know the injection profile of the steam entering the formation through the perforations in the well casing. Also, it is desirable to know the quality of the steam actually entering the formation so that the BTU input to the formation can be determined. The efficiency of the recovery can be calculated and steps taken to improve that efficiency.

The above referenced patent describes a method by which the quality of the steam entering a formation may be measured. The apparatus includes a wire bristle arrangement which is used to separate the liquid from the vapor in the steam and permit the measurement of the quantity of liquid separately from the vapor. This permits one to determine the actual quality of the steam at the point of injection. Also, the apparatus can be used to determine the quality of steam at various depths in the wellbore and thus the actual profile of the steam quality can be accurately measured.

The '627 patent relies upon a wire bristle arrangement in which the bristles bear against the inner wall of the well casing to separate the water from the vapor and funnel the water toward the center of the apparatus. The patent discloses a bristle arrangement in which individual wire bristles are clamped to a mandrel arrangement to provide an arrangement in which the bristles project radially outward from the mandrel. The overall diameter of the bristle arrangement is larger than the diameter of the well casing so that as the bristle arrangement is lowered into the well casing the bristles will bend upwardly and thus funnel the liquid that is separated from the vapor toward the center of the instrument. The bristles are deformed into a cusped-shaped convex upward as the tool is lowered into the well. Conversely, as the tool is pulled up the casing, the bristles invert and form an umbrella-shaped region convex downward. As vapor and liquid flow through the bristles, the drag force caused by fluid flow depends on the vapor and liquid flow rates and upon whether the bristles are pointing "up" or "down." In the former case, total drag depends more strongly on liquid flow rate, since the liquid path is more drastically altered.

The '627 patent discloses the use of braided stainless wire for forming the individual bristles. The individual bristles are attached by either welding their inner ends to the mandrel or clamping them to the mandrel by suitable means. As explained in the patent, the use of welding to attach the bristles to the mandrel or central assembly of the tool is not desirable since the heat of welding affects the mechanical properties of the bristles and reduces their effectiveness. While clamping overcomes the effects of welding, it does pose a problem in distributing the bristles in a uniform arrangement around the mandrel. The multiple rows of bristles also require a complicated clamping arrangement to properly space the individual rows of bristles and provide a uniform bristle arrangement that will separate all of the liquid from the vapor.

Accordingly, the present invention is directed to overcoming these and other problems experienced by the prior art.

SUMMARY OF THE INVENTION

The present invention solves the above problems by providing a unique method for forming the bristles. In particular, the method comprises utilizing a flat sheet of relatively thin metal and then slotting the metal to provide the individual bristles. The slots are uniformly spaced and extend from one edge of the sheet to the adjacent side but terminate short of the edge. This provides a narrow edge for connecting the individual bristles together. After the sheet is slotted the unslotted portion of the sheet is bent at right angles to the slotted portion to form a flange. This flange is then rolled into a cylinder and the edge is secured to provide an individual row of bristles. Multiple rows of the bristles can then be stacked and mounted on a suitable mandrel to provide the required bristle assembly.

From the above brief description of the invention it will be appreciated that the individual bristles are all of a uniform size and equally spaced from each other. Further, the bristles all extend equal distances outward from the mandrel. By mounting multiple rows of the bristles on a mandrel one can provide a bristle assembly in which the bristles are all uniform size and uniformly positioned. Thus, the assembly will have a high efficiency for separating the liquid from the vapor as described in the above referenced patent.

The bristles can be sized and arranged as called for in the '627 patent to form a network that extends across substantially the entire cross sectional area of the well casing at the location of the bristles. Using the bristle assembly of the present invention it is easy to position the bristles of the individual rows of bristles so that they overlap each other and substantially cover the entire cross sectional area of the well casing. The use of flat bristles instead of round wire ones also assists in separating the liquid from the vapor and reduces the force required for reversing the bristles from an upward pointing direction to a downward direction as described in the '627 patent.

Various materials may be used for the bristles but preferably, a spring material is used to provide the action desired from the bristle assembly. In particular, non-corrosive spring-like metals, for example stainless steel, INCONEL ® (a nickel-chromium-iron alloy manufactured by Cabot Corporation) and HASTEL- LOY ® (a nickel-chromium-molybdenum-tungsten-iron alloy manufactured by Cabot Corporation) are preferred.

Other purposes, distinctions over the art, advantages and features of the invention will be apparent to one skilled in the art upon review of the following.

BRIEF DESCRIPTION OF THE DRAWINGS

The actual construction, operation, and the apparent advantages of the present invention will be better understood by referring to the drawings in which like numerals identify like parts and in which.

DESCRIPTION OF THE PREFERRED EMBODIMENT

Figure 1:
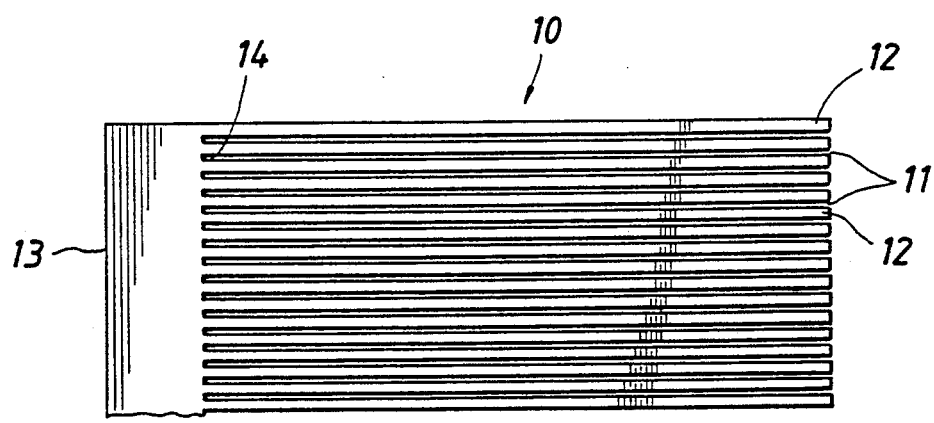
FIG. 1 is a view of a portion of a sheet showing the slots which are used to form the individual bristles of the assembly.

Referring to FIG. 1, there is shown a portion of the flat sheet used for forming one row or layer of bristles of the assembly. The sheet 10 is properly sized so that when the flange is rolled into a cylindrical configuration the overall diameter of the bristles will be the desired diameter. As explained above, the sheet preferably is non-corrosive metal material that is relatively thin but has good spring action. It has been found that when constructing a bristle assembly for the instrument described in patent '627 for running in a 6.366-inch casing, material having a thickness of 0.007 inches is satisfactory. For this size assembly the bristles should extend 3.411 inches from the flange and the sheet should be 4.0237 inches by 3.938 inches, for a 1.0-inch diameter tool body.

A plurality of individual slots 11 are formed in the material with the slots extending from the right hand edge to a position 14 adjacent the left hand edge 13 of the material. The slots are all of uniform width and length and are parallel to each other. Further, the slots are equally spaced to provide a plurality of uniform bristles 12 extending from the solid portion of the sheet at the left hand edge. The slots should have a length slightly longer than the desired length of the bristles to allow a portion of the slot to extend up into the flange when the material is bent. This greatly facilitates the rolling of the flange into a cylindrical arrangement. For the example given above, it has been found satisfactory to extend the slots for a distance of 3.437 inches when using 4.000-inch wide material having 0.007-inch thickness.

While the slots can be formed by various machining procedures, it is preferable to stack a large number of pre-cut sheets and clamp them together. The slots can then be easily machined by electric arc discharge machining to provide uniform slots with equal spacing. Since a large number of sheets are machined at the same time the overall cost of a single sheet or row of bristles is very low.

Figure 2:
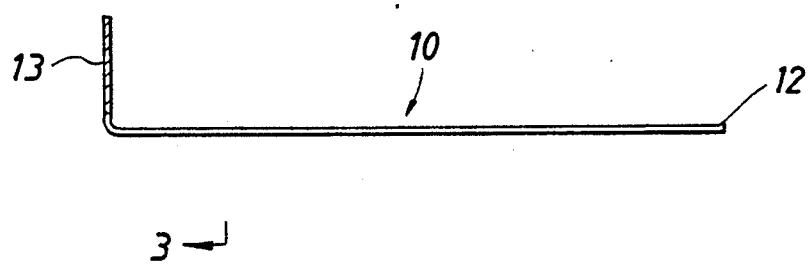
FIG. 2 is an end view of the member shown in FIG. 1 with the flange bent upward on end.
Figure 3:
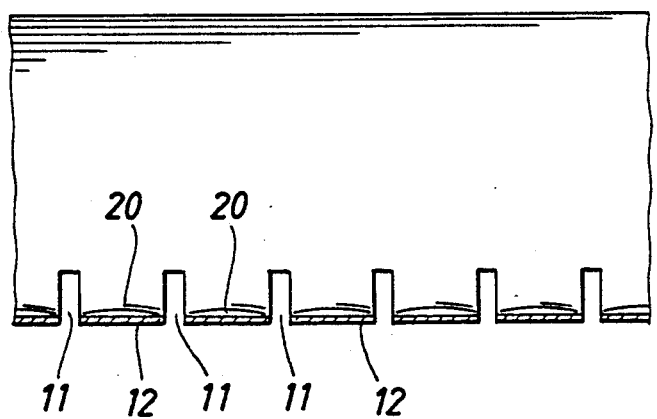
FIG. 3 is a section along line 3—3 of FIG. 2.

Referring to FIG. 2, there is shown the slotted sheet shown in FIG. 1 with the flange with portion 13 bent upward at right angles to form the flange on the member. The flange has a width of 0.612 inches while having bristles of a length of 3.411 inches measured from the surface 14 of the flange. The portion 13 is preferably bent using a conventional brake and a rubber pad to provide a rounded corner and in addition, provide a slight curve or deflection in each individual bristle as shown at 20 in the section of FIG. 3. In particular, the portion of the bristle which occupies the first position in the radius of the bend assumes the slightly concave shape 20 as shown in FIG. 3. The slightly concave section greatly strengthens the bristles in the bend radius and also increases the stiffness of the spring of the bristle. This also prevents breakage of the bristle at the bond point when bonding. Also, in FIG. 3, the individual slots 11 clearly extend upward into the flange member, preferably about 0.057 inches.

Figure 4:
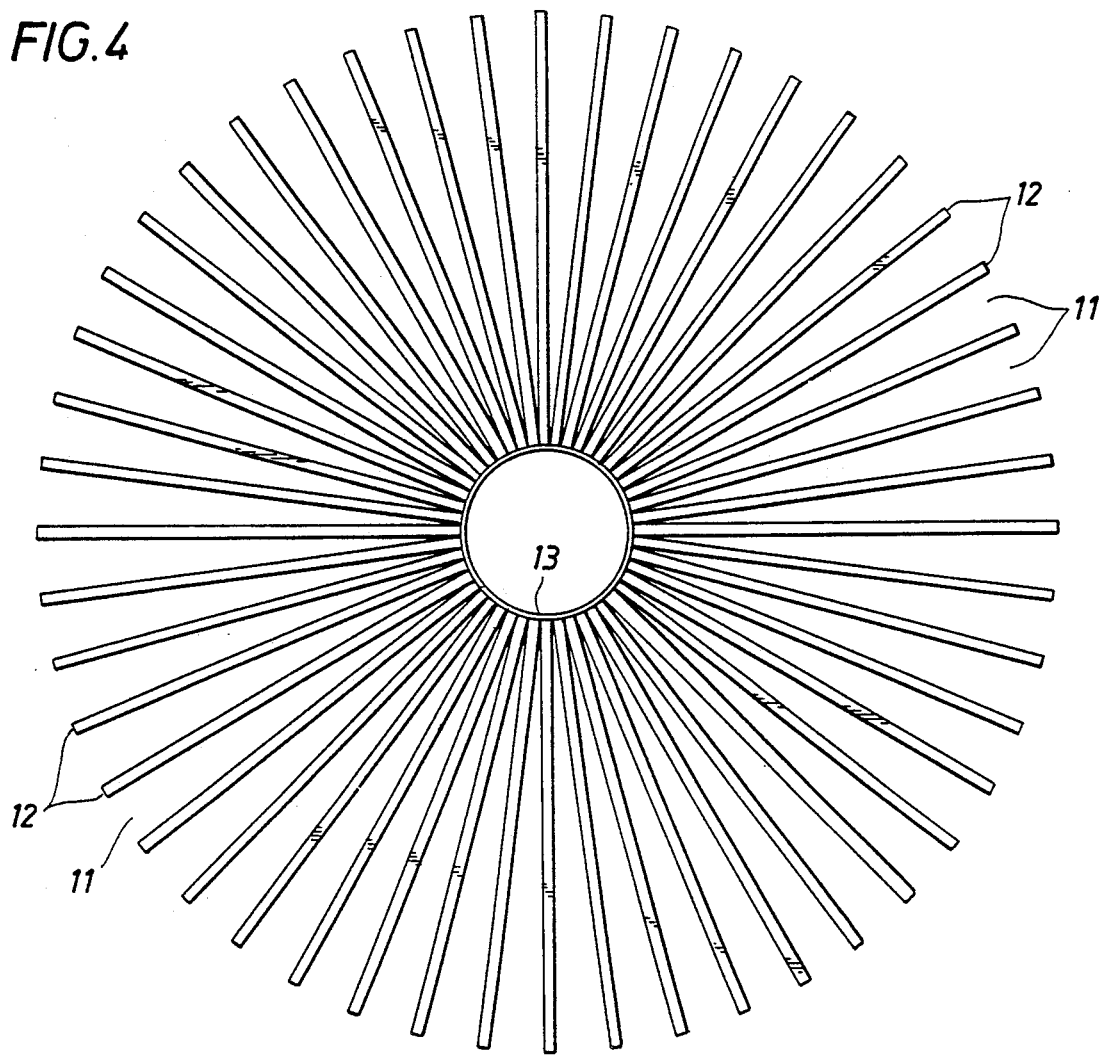
FIG. 4 is a larger section of the bristle assembly showing the flange bent upward and rolled into a circular configuration.
Figure 5:
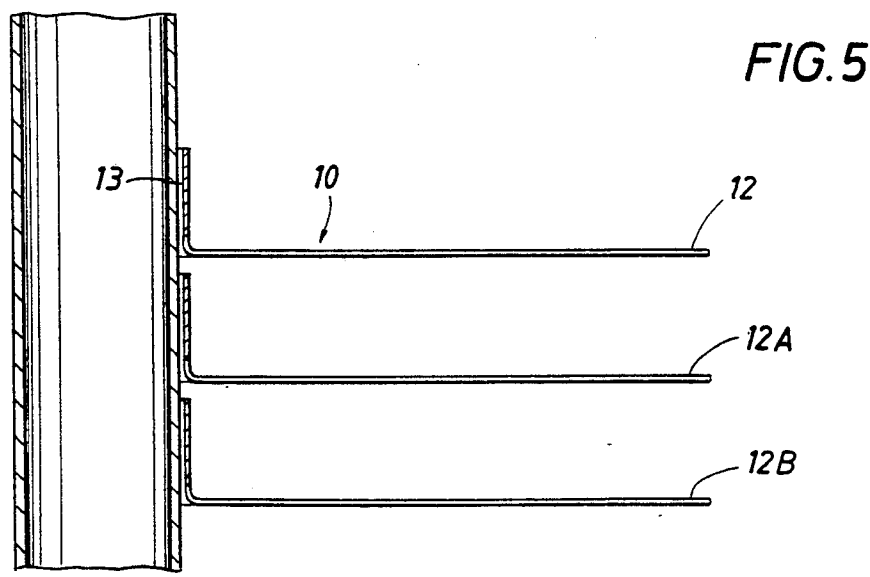
FIG. 5 is a view of a plurality of cylindrical members.

Referring to FIG. 4, there is shown a larger section of the material used for forming the bristle arrangement rolled into a cylindrical configuration. In particular, it is seen that as the member is rolled into the cylindrical configuration the outer ends of the bristles separate into a fan-like arrangement and the edges of the cylinder may be fastened together or it may be clamped in position. The use of several rows of bristles shown in FIG. 4 will permit the individual bristles to overlap each other and cover the complete cross sectional area of the well casing.

While various configurations of bristles may be formed using various thicknesses of material, and the bristles may have various lengths, it has been found desirable that the bristles have an overall length-to-width ratio of between about 40 and 70. Similarly, it has been found desirable for the ratio of the width of the bristle to the thickness of the material be between about 5 and 20. By maintaining these ratios, bristles suitable for forming the liquid separating means described in patent '627 will be obtained. The width of the flange may be approximately 5 to 20 percent of the length of the bristles. Once the flange width and the length of the bristles are obtained, one can determine the overall width of the material while the length will be determined by the circumference of the cylindrical member on which the individual rows of bristles are mounted. While HASTELLOY ® has been found to be a satisfactory material, obviously other non-corrosive material such as stainless steel, aluminum, bronze or INCONEL ® can also be used.

The foregoing description of the invention is merely intended to be explanatory thereof, and various changes in the details of the described method and bristle assembly may be made within the scope of the appended claims without departing from the spirit of the invention.

What is claimed is:

1. A bristle assembly comprising:
a circular shaped array of uniformly spaced bristles bent to extend radially outward from one end of a cylindrical flange, each bristle being separated from an adjacent bristle by a slot which extends into the flange past a location where the bristle is bent.

2. The bristle assembly of claim 1 including a plurality of arrays of bristles stacked on a support member.

3. The bristle assembly of claim 1 wherein each bristle has a concave shape in the area adjacent to the cylindrical flange.

4. The bristle assembly of claim 1 wherein each bristle has an overall length-to-width ratio of 40-70 and a width-to-thickness ratio of 5-20.

5. The bristle assembly of claim 1 wherein the bristles and flange are a single piece of formed sheet metal.

* * * * *